(12) United States Patent
Anvar et al.

(10) Patent No.: US 7,611,671 B2
(45) Date of Patent: Nov. 3, 2009

(54) REDUCTION OF CARBON MONOXIDE INTERFERENCE IN GASEOUS ANALYTE DETECTORS

(75) Inventors: David J. Anvar, Sunnyvale, CA (US);
David J. Chazan, Palo Alto, CA (US);
Bryan P. Flaherty, Half Moon Bay, CA (US); Bhairavi R. Parikh, Palo Alto, CA (US)

(73) Assignee: Aperon Biosystems Corp., Menlo Park, CA (US)

( * ) Notice: Subject to any disclaimer, the term of this patent is extended or adjusted under 35 U.S.C. 154(b) by 630 days.

(21) Appl. No.: 11/250,958

(22) Filed: Oct. 14, 2005

(65) Prior Publication Data

US 2007/0086920 A1    Apr. 19, 2007

(51) Int. Cl.
*G01N 33/497* (2006.01)
(52) U.S. Cl. ............... 422/83; 422/87; 436/116; 436/118; 436/167; 73/23.2; 73/31.02
(58) Field of Classification Search ............. 422/83–88; 73/23.2, 31.02, 31.03; 436/167, 900, 116, 436/118
See application file for complete search history.

(56) References Cited

U.S. PATENT DOCUMENTS

| | | | |
|---|---|---|---|
| 3,674,435 A * | 7/1972 | Van Luik Jr. et al | 436/36 |
| 3,842,159 A * | 10/1974 | Niebylski et al. | 423/213.5 |
| 4,302,315 A * | 11/1981 | Stetter et al. | 204/412 |
| 4,406,770 A * | 9/1983 | Chan et al. | 204/406 |
| 4,633,704 A * | 1/1987 | Tantram et al. | 73/31.05 |
| 4,818,745 A | 4/1989 | Kolts | |
| 5,795,787 A | 8/1998 | Silkoff et al. | |
| 5,955,214 A | 9/1999 | Bellows et al. | |
| 6,010,459 A | 1/2000 | Silkoff et al. | |
| 6,113,869 A | 9/2000 | Jain et al. | |
| 6,203,596 B1 | 3/2001 | Von Gemmingen | |

(Continued)

FOREIGN PATENT DOCUMENTS

EP        0750933 A1    2/1997

OTHER PUBLICATIONS

Rodkey, F. Lee et al.; "Release of carbon monoxide from acrylic and polycarbonate plastics"; 1969, *Journal of Applied Physiology*, vol. 27, No. 4, pp. 554-555.

*Primary Examiner*—Lyle A Alexander
(74) *Attorney, Agent, or Firm*—Townsend and Townsend and Crew LLP.; M. Henry Heines (57) ABSTRACT

Highly sensitive devices for detecting nitric oxide and/or other gaseous analytes in gaseous samples are improved by the incorporation of a carbon monoxide scavenger in the interior of the device or in the device packaging. The release of carbon monoxide within the housing of the device by the plastic used in the construction of the housing or by anything within the device that releases carbon monoxide causes a loss in sensitivity due to competition between the carbon monoxide and the nitric oxide for the binding sites on the device sensor. The scavenger corrects this by either catalyzing the oxidation of carbon monoxide to the less competitive carbon dioxide or immobilizing the carbon monoxide by affinity-type or covalent binding. Analogous effects are achieved for analytes other than nitric oxide but that likewise encounter interference from carbon monoxide in binding to sensors.

15 Claims, 5 Drawing Sheets

U.S. PATENT DOCUMENTS

| | | | |
|---|---|---|---|
| 6,404,205 B1 * | 6/2002 | Kitamura | 324/464 |
| 6,849,239 B2 | 2/2005 | Morris | |
| 6,855,297 B2 | 2/2005 | Van Den Bussche et al. | |
| 2004/0017570 A1 | 1/2004 | Parikh et al. | |
| 2005/0053549 A1 | 3/2005 | Parikh et al. | |
| 2005/0083527 A1 | 4/2005 | Flaherty et al. | |
| 2005/0126930 A1 | 6/2005 | Prohaska et al. | |

* cited by examiner

REDUCTION OF CARBON MONOXIDE INTERFERENCE IN GASEOUS ANALYTE DETECTORS

BACKGROUND OF THE INVENTION

1. Field of the Invention

This invention lies in the field of high-sensitivity gas analysis.

2. Description of the Prior Art

Persons suffering from asthma are able to monitor the intensity of their condition and to predict the likelihood of an asthmatic attack by monitoring the level of nitric oxide (NO) in their exhaled breath. Sensors that detect nitric oxide levels in exhaled breath are disclosed in U.S. Pat. No. 5,795,787, issued Aug. 18, 1998, U.S. Pat. No. 6,010,459, issued Jan. 4, 2000, United States Pre-Grant Publication No. US 2004-0017570 A1, published Jan. 29, 2004, United States Pre-Grant Publication No. US 2005-0083527 A1, published Apr. 21, 2005, and United States Pre-Grant Publication No. US 2005-0053549 A1, published Mar. 10, 2005. Each of these documents is incorporated herein by reference in its entirety. The sensors described in these documents are contained in devices with flow-through passageways for retention of nitric oxide-binding materials, allowing the user to exhale into the device and obtain a reading from the device that indicates the nitric oxide level in the exhaled breath. The sensors themselves use sophisticated sol-gel technology in conjunction with nitric oxide biding agents such as cytochrome C and other proteins that bind nitric oxide upon contact and undergo optically detectable changes, most notably optical absorption, when such binding occurs. The sensors that have been developed under this technology are sensitive enough to detect nitric oxide in the parts-per-billion range.

Such a high level of sensitivity makes the sensors vulnerable to interferents that are present in extremely low quantities, including gaseous interferents that are emitted from the materials of construction of the device itself. It has indeed been discovered that monitoring devices that contain these sensors in certain polymeric housings, notably housings made from acrylic resins, display a gradual loss in sensitivity over time. The loss in sensitivity limits the shelf lives of these devices and hence the suitability of these devices for long-term storage for purposes of long-distance shipping and for the building of inventories adequate to meet growing or fluctuating demands. This loss of sensitivity is due to the emission of low levels of carbon monoxide by the polymeric material from which the device housing is constructed. The reason for the carbon monoxide emission is unknown, and may be a de-gassing of the polymer to release dissolved carbon monoxide, a decomposition of additives included in the polymer, or a decomposition of the polymer itself. Each of the terms "emission" and "release" is used herein to generically cover all of these possible mechanisms. Regardless of the reason for the emission, the cumulative adsorption of the emitted carbon monoxide by the sensing material is believed to cause a reduction in the binding sites available for nitric oxide. While not asserting this explanation is incontestable, the inventors herein offer it as a possible explanation for the loss in sensitivity. Similar concerns arise with other nitric oxide sensing devices that are constructed with carbon monoxide-emitting polymers, including devices that are designed for atmospheric testing or for physiological testing other than exhaled breath, such as nasal emissions. In many of these devices, nitric oxide detection is needed at concentrations higher than those encountered in the exhaled breath of an individual suffering from asthma. Nevertheless, these devices can also be susceptible to a loss of sensitivity for the same reasons as the exhaled breath analyzers cited above.

The prior art recognizes the existence of transition metal oxides that can catalyze the oxidation of carbon monoxide to carbon dioxide, and it is also known that carbon dioxide does not bind to proteins with the same affinity as carbon monoxide. Disclosures of these metal oxides and their use as oxidation catalysts appear in U.S. Pat. No. 4,818,745, issued Apr. 4, 1989, U.S. Pat. No. 5,955,214, issued Sep. 21, 1999, U.S. Pat. No. 6,113,869, issued Sep. 5, 2000, U.S. Pat. No. 6,203,596 B1, issued Mar. 20, 2001, and U.S. Pat. No. 6,855,297 B2, issued Feb. 15, 2005. Each of these documents is likewise incorporated herein by reference in its entirety. The same metal oxides can catalyze the oxidation of nitric oxide to nitrogen dioxide ($NO_2$), however. Accordingly, the removal of the interferent by oxidation can also be expected to cause removal of the analyte and therefore to interfere with the nitric oxide detection.

SUMMARY OF THE INVENTION

These and other matters are addressed by the present invention, which resides in improvements in devices for detecting trace amounts of nitric oxide and/or other gaseous analytes in gas samples by sensors that are susceptible to interference from carbon monoxide. Gases in which nitric oxide detection is desirable for various reasons include breath, exhaled through the mouth or nose, atmospheric air, automotive emissions, industrial plant emissions, and air in residential, commercial, and industrial environments in general. Other gaseous analytes are likewise of interest for detection at very low levels. Molecular oxygen is one such analyte. While molecular oxygen can be detected on the basis of its ability to bind to hemoglobin and other species that contain the same binding groups as hemoglobin, these groups are likewise susceptible to interference from carbon monoxide in the same manner as the groups that bind nitric oxide.

The device to be improved is one that contains an immobilized, non-gaseous binding agent, referred to herein as a sensor, that binds the analyte of interest and is illustrated by the sensors of the reference documents cited. The typical sensor for a nitric oxide detector is capable of binding both nitric oxide and carbon monoxide from gaseous mixtures upon contact and is contained in a housing of a polymeric material that releases carbon monoxide at very low concentrations. In general, interference from carbon monoxide can arise in a housing that is constructed of a carbon monoxide-releasing material, or it can arise from a carbon monoxide-releasing component that is enclosed within the housing. The improvement presented by this invention is the placement of a carbon monoxide scavenger in the device, or in packaging containing the device, in a manner that provides gas diffusion access to the scavenger from the carbon monoxide-releasing material or component. The term "carbon monoxide scavenger" is used herein to represent any agent that either immobilizes carbon monoxide by binding, and thereby extracts the carbon monoxide from the adjacent atmosphere, or converts carbon monoxide to a species that does not compete with the analyte for binding to the sensor. For scavengers at which conversion occurs, the most typical conversion is an oxidation reaction converting carbon monoxide to carbon dioxide, the scavenger thus functioning as an oxidation catalyst. Certain scavengers will function as an oxidation catalyst when oxygen is present and as a simple binding agent when oxygen is not present. When functioning as a catalyst, the scavenger is a renewable agent capable of the conversion of an unlimited number of carbon monoxide molecules. When functioning as a binding agent, the scavenger is consumed by the carbon monoxide and can be depleted of accessible binding sites.

In devices that contain a housing formed of a carbon monoxide-releasing polymer, the scavenger can be positioned inside the housing in a manner that provides diffusional access between the scavenger and the interior surfaces of the housing, and particularly those interior surfaces that also have diffusional access to the sensor. For devices that are enclosed in sealed packages and stored in packaged form for extended periods of time or for transport, the scavenger can be placed in the packaging in proximity with the device rather than inside the device housing. The scavenger in this arrangement will likewise draw the carbon monoxide from the atmosphere, lowering or preventing the accumulation of carbon monoxide both in the atmosphere and within the device itself and thereby controlling any carbon monoxide interference at the sensor. In all of these embodiments, the scavenger consumes carbon monoxide emitted within or by the housing, thereby maintaining levels of carbon monoxide in the interior of the housing that are not detrimental to the performance of the sensor.

Other gaseous interferents that are emitted by one or more of the components of the device and that are removed or converted by the scavenger are likewise reduced in concentration. Certain polymers, for example, emit hydrogen gas instead of, or in addition to, carbon monoxide. When the scavenger is an oxidation catalyst and oxygen is present, the scavenger can oxidize hydrogen gas that is emitted, thus reducing in concentration or eliminated by the catalyst as a result. In general, devices that incorporate a carbon monoxide scavenger as set forth herein do not suffer a loss of sensitivity over time and enjoy a shelf life of months, years, or indefinite periods of time.

Certain materials that are useful as carbon monoxide scavengers in the practice of this invention also interact with the analyte, either by binding to the analyte or converting the analyte to another species by oxidation or otherwise. When one of these materials is used as the scavenger, the sensitivity of the sensor toward the analyte can thus be compromised if the scavenger draws analyte away from the sensor. Thus, while the scavenger reduces competitive binding at the sensor, it can also reduce the amount of analyte that reaches the sensor. This can occur, for example, when the analyte is nitric oxide and the scavenger is an oxidation catalyst such as a metal oxide, since such a scavenger will either bind or oxidize both the nitric oxide and the carbon monoxide. This can be prevented from occurring to any significant degree by constructing the device in any of several ways. For example, the scavenger and the sensor can be separated by a spatial distance that will minimize any diffusion of the analyte from the sensor to the scavenger. Alternatively, a diffusion-limiting component such as a membrane or an orifice can be placed between the catalyst and the binding agent. In either case, any reduction in the analyte binding at the sensor that is attributable to the presence of the scavenger can be limited to a maximum of 1 ppb by volume of absolute amount of analyte or 10% by volume of the analyte level detected, whichever is greater. This will be true despite the fact that there are passageways between the scavenger and the sensor through which gas can diffuse.

These and other objects, features and advantages of the invention are better understood from the descriptions that follow.

DETAILED DESCRIPTION OF THE INVENTION

As noted above, carbon monoxide scavengers for use in the practice of the present invention include any chemical agent or component that extracts carbon monoxide from the surrounding atmosphere and either immobilizes the extracted carbon monoxide by binding, whether affinity-type or covalent, or converts the carbon monoxide to a species that is significantly less of an interferent at the sensor for the detection of the analyte. One group of scavengers that meet this description are carbon monoxide oxidation catalysts. Such catalysts are known in the art and include a variety of metals and metal oxides. Prominent among these are transition metal oxides, and the most frequently reported examples are oxides of manganese, copper, nickel, and mixtures of two or more of these metals. These oxides and mixtures can also be used in combination with oxides of silver, iron, tin, and various other metals. Other metals that serve as catalysts for the oxidation of carbon monoxide are indium and bismuth, used either alone or in combination with one or more transition metal oxides. Of the transition metal oxides, mixtures of manganese dioxide and cupric oxide are preferred. These mixtures are available as a variety of commercial products. One class of products is designated by the name CARULITE®, including CARULITE 150, CARULITE 200, CARULITE 300, and others. Products within this class contain about 60-75% manganese dioxide, about 11-14% cupric oxide, and about 15-16% alumina, all by weight. Another known product is HOPCALITE, which contains about 60% manganese dioxide and about 40% cupric oxide, all by weight. CARULITE products and HOPCALITE are both available from Carus Chemical Co., Peru, Ill., USA. The metal oxide or metal oxide mixture will generally be in solid form, such as a powder, granule, pellet, extrudate, mesh screen, or coating, and can be used either in undiluted or unsupported form or supported on an inert catalyst support such as a porous granule or screen. Such forms are well known in the field of heterogeneous catalysis. While these materials are known as oxidation catalysts and so referred to herein, they also function as scavengers in a non-catalytic manner when oxygen or oxidizing agents in general are excluded from the environment, by direct reaction with the carbon monoxide. These metals and metal oxides are nevertheless referred to herein as "catalysts" for convenience to reflect the fact that these materials are indeed catalysts even though they may not be functioning as such in all environments to which the present invention applies.

The amount of carbon monoxide scavenger utilized in the practice of this invention is not critical to the invention and can vary widely. Any amount that is sufficient to reduce or eliminate the loss in sensitivity of the sensor over time, by drawing carbon monoxide from the interior of the device or from the atmosphere surrounding the device at a sufficient rate to prevent the accumulation of the carbon monoxide in the interior of the housing and particularly in the vicinity of the sensor, will be effective. In most cases, this can be achieved by using a small amount of the scavenger relative to the carbon monoxide-releasing material. For embodiments in which the carbon monoxide-releasing material is a polymeric material from which the housing of the device is constructed, effective results can be achieved by use of a scavenger in the form of a granulated solid that constitutes from about 0.005 to about 0.3 part by weight of the granulated solid per 100 parts by weight of the polymeric material in the housing. A narrower range is about 0.01 to about 0.1 part by weight per 100 parts by weight of the polymeric material in the housing. The choice of scavenger amount can be influenced by factors such as the inclusion or absence of diffusion-limiting components such as a membrane or orifice, or the atmosphere inside the device. In devices designed for detecting nitric oxide and that utilize a metal oxide as the scavenger, one factor in determining the optimal amount of the scavenger is whether oxygen is permitted in or excluded from the device, i.e., whether the scavenger functions primarily as a carbon monoxide oxidation catalyst or as a carbon monoxide binding agent. When functioning primarily as a catalyst, a lesser amount can be used since the scavenger will not be consumed by the carbon monoxide.

In embodiments of the invention in which the scavenger is placed in the interior of the device, the location of the scavenger is chosen such that any gases emitted within the device that will compete with the analyte for binding to the sensor have diffusional access to, i.e., can diffuse through the interior of the housing to, the scavenger. The terms "diffusional access" and "accessible to gaseous diffusion" are used herein to denote the exposure of the scavenger or the sensor to all internal cavities and passageways through which gaseous components can diffuse, so that any components present in these cavities or passageways or released into them by surfaces or walls that border the cavities or passageways have a diffusion path through gas to the scavenger or sensor. Gaseous species, again notably carbon monoxide, in the cavities or passageways that might affect the sensor are thus continually drawn away from the sensor toward the scavenger, and accumulation of these components within the housing is avoided by the concentration gradient created by the scavenger due to the consumption of the components by the scavenger. Carbon monoxide molecules that become bound to the sensor are readily dissociated from the sensor and released back into the adjacent gas mixture when the gas is depleted of carbon monoxide. The tendency of the gas composition toward equilibrium thus helps to maintain a low level of carbon monoxide binding at the sensor, thereby promoting reliability and reproducibility.

The lowering of the carbon monoxide level by the scavenger is thus diffusion controlled and occurs continually over the shelf life of the device. The binding of analyte to the sensor, by contrast, occurs during forced convection over the few seconds during which the gas sample is drawn or forced into the device. This, plus the diffusion of the analyte in the sample toward the sensor and the reaction between the analyte and the sensor, all occurs within a time span of at most a few minutes, as compared to the extended time period over which carbon monoxide is released, during storage for example. This difference in time scale reduces the number of interactions between the scavenger and the analyte that might affect the analysis, or avoids any significant degree of such interaction. As noted above, one method of minimizing the occurrence of this interaction is by placing the scavenger at a sufficient distance from the sensor that no more than an insignificant amount of the analyte will migrate from the sensor to the scavenger during the duration of the analysis. The distance can thus be at least 3 mm, preferably from about 3 mm to about 300 mm, and most preferably from about 10 mm to about 100 mm. In a presently preferred embodiment in which the analyte is nitric oxide, the sensor and scavenger are separated by a diffusion path of about 45 mm in length. Baffles or particles can be placed in the diffusion path to further reduce the linear diffusion speed. In embodiments in which the diffusion of the analyte toward the scavenger is limited by an obstruction such as a diffusion-lowering membrane or a flow-restricting orifice, a smaller distance between sensor and scavenger will achieve the same result. The goal in all embodiments is to limit any variation in the analyte detection that is caused by the scavenger to less than 1 ppb of the analyte (in absolute terms) or less than about 10% of the analyte level detected in the sample, whichever is greater. All references to ppm, ppb, or percent in this specification and the appended claims, when referring to components of gas mixtures, are by volume. In embodiments in which granulated filler particles are placed in the diffusion path, a preferred granulated filler is a molecular sieve material that also provides humidity control.

Certain polymeric materials are known to release carbon monoxide at levels that will affect sensors that operate in the parts-per-million and parts-per-billion ranges. Examples of these materials are acrylics, polycarbonates, polypropylenes, and cyclic polyolefin copolymers. Acrylics include polymers or copolymers of acrylic acid, methacrylic acid, esters of acrylic and methacrylic acids, and acrylonitrile. Examples are PLEXIGLAS® (Rohm & Haas), LUCITE® (DuPont), and ACRYLITE® (Cyro Industries). Examples of polycarbonates are LEXAN® (GE Plastics), CALIBRE™ (Dow Chemical Company), and MAKROLON® (Bayer AG). An example of a cyclic polyolefin copolymer is TOPAS® (Ticona Engineering Polymers, Florence, Ky., USA). The rate of carbon monoxide emission may vary among different lots or preparations of any of these polymers, and certain samples may produce no emissions at all, or emissions below the levels of detection. Emission levels are readily determined by conventional gas chromatography. Examples of these determinations for acrylic and polycarbonate plastics are provided by Rodkey, F. L., et al., "Release of carbon monoxide from acrylic and polycarbonate plastics," *J. Appl. Physiol.* 27(4): 554-555 (October 1969).

For devices within the scope of this invention that are designed for detection of nitric oxide (NO), any of a variety of known NO-binding agents that undergo a detectable, and preferably measurable, change upon binding NO can be used as the sensor. Examples of these binding agents are disclosed in the documents cited above in the "Description of the Prior Art." These examples include cytochrome C, hemoglobin in any of its oxidation states, myoglobin in any of its oxidation states, proteins that contain porphyrin groups, dye-labeled analogs of any of the aforementioned proteins, and NO-binding fragments of any of the aforementioned proteins. The binding agent can be mounted in a support matrix that immobilizes the agent and yet renders the agent accessible to gas mixtures for binding upon contact. Examples are sol gels, ormosils, polyvinyl alcohol, polymethylmethacrylate, and polydimethylsiloxane.

The change that is undergone by the sensor upon binding the analyte can be one that is detectable only by machine reading or one that is detectable by the naked eye, with or without comparison to standards, and with or without calibration. Optically detectable changes are preferred, including changes in absorbance, transmission, reflectance, fluorescence, and chemiluminescence. Sensors and matrices that exhibit changes in optical absorption are particularly preferred. Changes of an electrical nature can also be used, such as changes in electrical conductivity, impedance, electric current, and electric potential.

While devices in accordance with this invention are susceptible to a wide range of configurations and geometries, the invention as a whole can be understood by a detailed study of specific embodiments. Four such embodiments are shown in the drawings.

Figure 1:
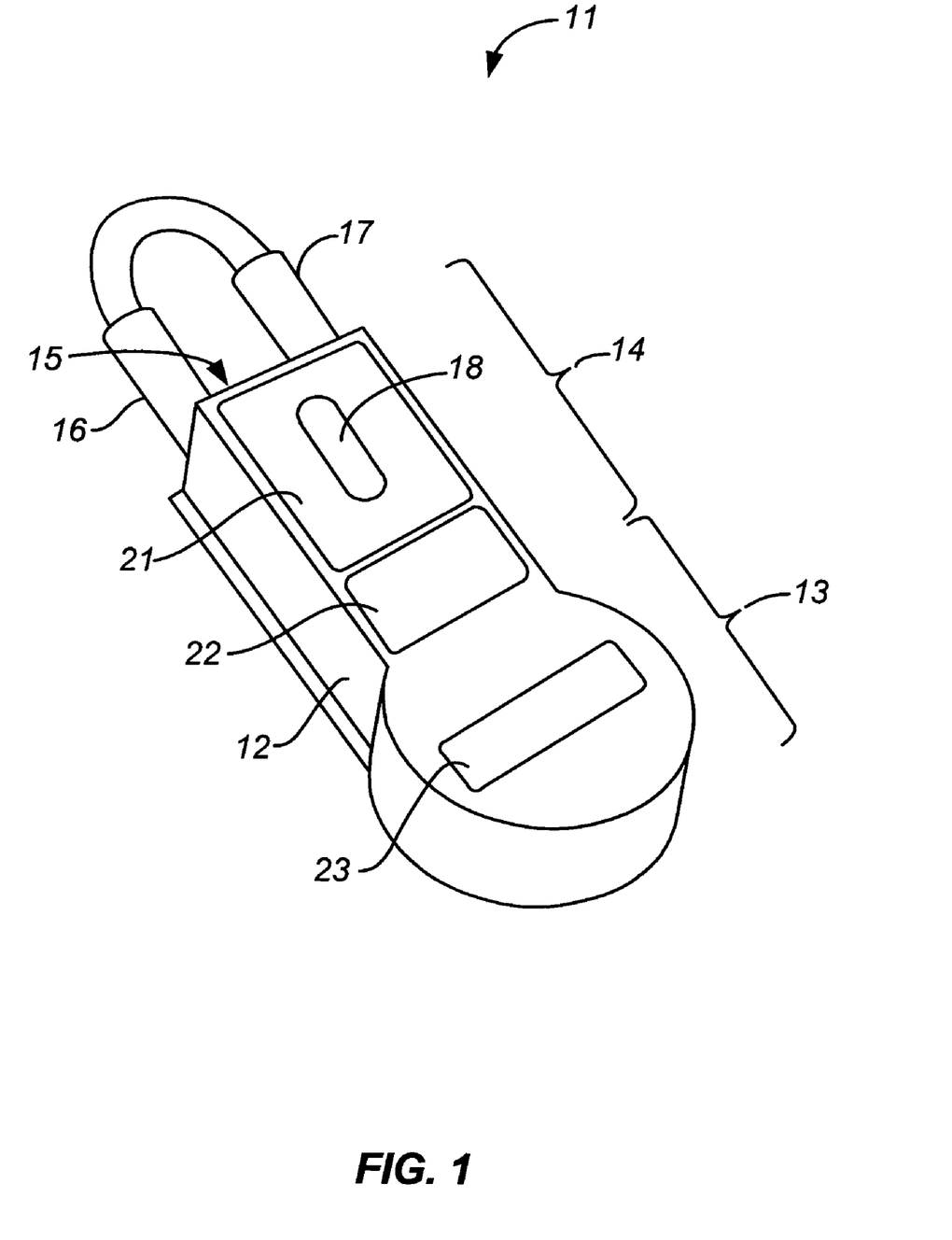
FIG. 1 is a perspective view of a device in accordance with the present invention.

The device 11 shown in the perspective view of FIG. 1 has a plastic housing 12 which is shaped to include an expanded end 13 by which the user can hold the device between thumb and forefinger, while the functional components reside in the body 14 of the device. An inlet port for the user to breathe into and an outlet port for displaced air to escape from the device are located in the end 15 of the device and not visible in this view. During storage and transportation, these ports are plugged by readily removable plugs 16, 17. The use of perforable aluminized tape is an alternative to the plugs; the tape can be perforated by the user immediately prior to use. A window 18 on the upper surface of the device provides access to the sensor as well as a reference for optical detection, and coverings 21, 22, 23 of paper or foil are adhered to the upper surface by adhesives, either for purposes of protection of for the display of indicia such as a manufacturer's logo, a serial number, or an expiration date.

Figure 2:
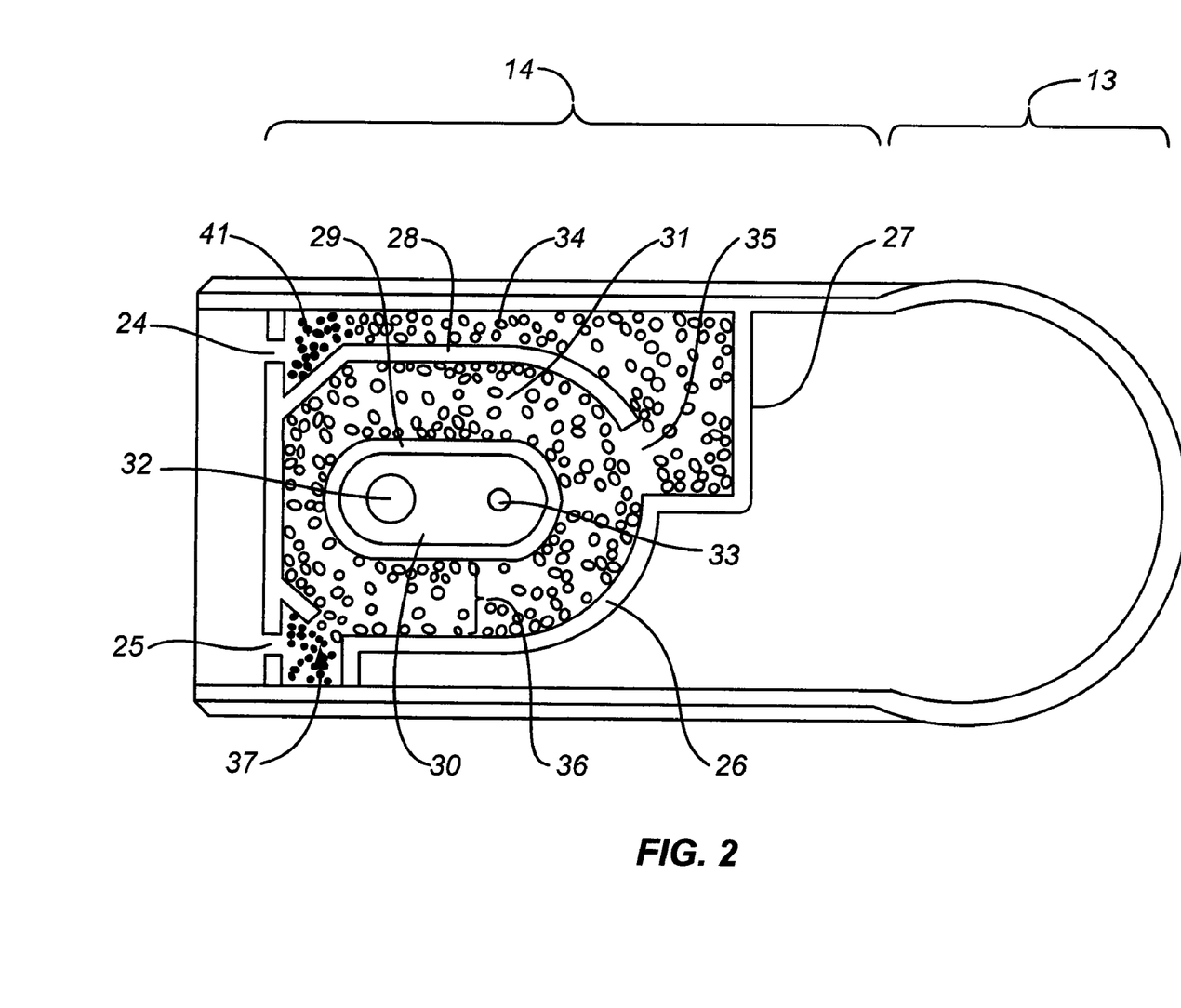
FIG. 2 is a planar view of the same device, showing the interior structure of the device.

FIG. 2 presents a top view with the coverings and plugs removed. Since the housing is transparent, the interior structure of the device is visible. The inlet port 24 and outlet port 25 are visible, as are a series of partitions that divide the interior into compartments and flow passages. The outer partitions 26, 27, 28 are gas blocking partitions that fully span the distance between the two flat portions (parallel to the plane of the drawing) of the device housing. These partitions block the passage of the gas sample, thereby retaining the sample within the functional regions of the device. A central partition 29 is bonded to only one of the two flat portions of the housing and leaves a gap at the other. With this gap, the central partition 29 only partially blocks the passage of the sample gas, allowing the gas to pass into the core region 30 of the device which contains the sensor. The internal cavities and passages are filled with a desiccant 31 to control the humidity in the interior of the device. A 3A Molecular Sieve is one example of a desiccant effective for this purpose. The sensor 32 is mounted inside the core region 30, close to a reference window 33. The path of travel of the gas sample through the device therefore begins at the inlet port 24, passes through a peripheral passage 34 between the external wall of the device and the outer partition 28, then through an opening 35 into an intermediate region 36 surrounding the core region 30, and then over the central partition 29 (through the gap, which is not shown) into the core region 30 where the sample contacts the sensor 32. Air that is displaced by the sample is expelled from the device through an opening 37 in the outer partition 26 and from there through the outlet port 25.

The carbon monoxide scavenger 41 is retained in the inlet region adjacent to the inlet port 24, and is sufficiently separated from the sensor to prevent the scavenger from drawing significant amounts of nitric oxide from the region surrounding the sensor 32. The separation in this case is established by the diffusion path extending through the desiccant particles in the peripheral passage 34, the opening 35, and the intermediate region 36. The surfaces of the housing that can release carbon monoxide are those of the flat upper and lower portions of the housing (parallel to the plane of the drawing) and each of the various partitions and peripheral walls of the housing. Alternatively, the scavenger can be retained in the outlet region adjacent to the outlet port 25, or in both the inlet and outlet regions.

Figure 3:
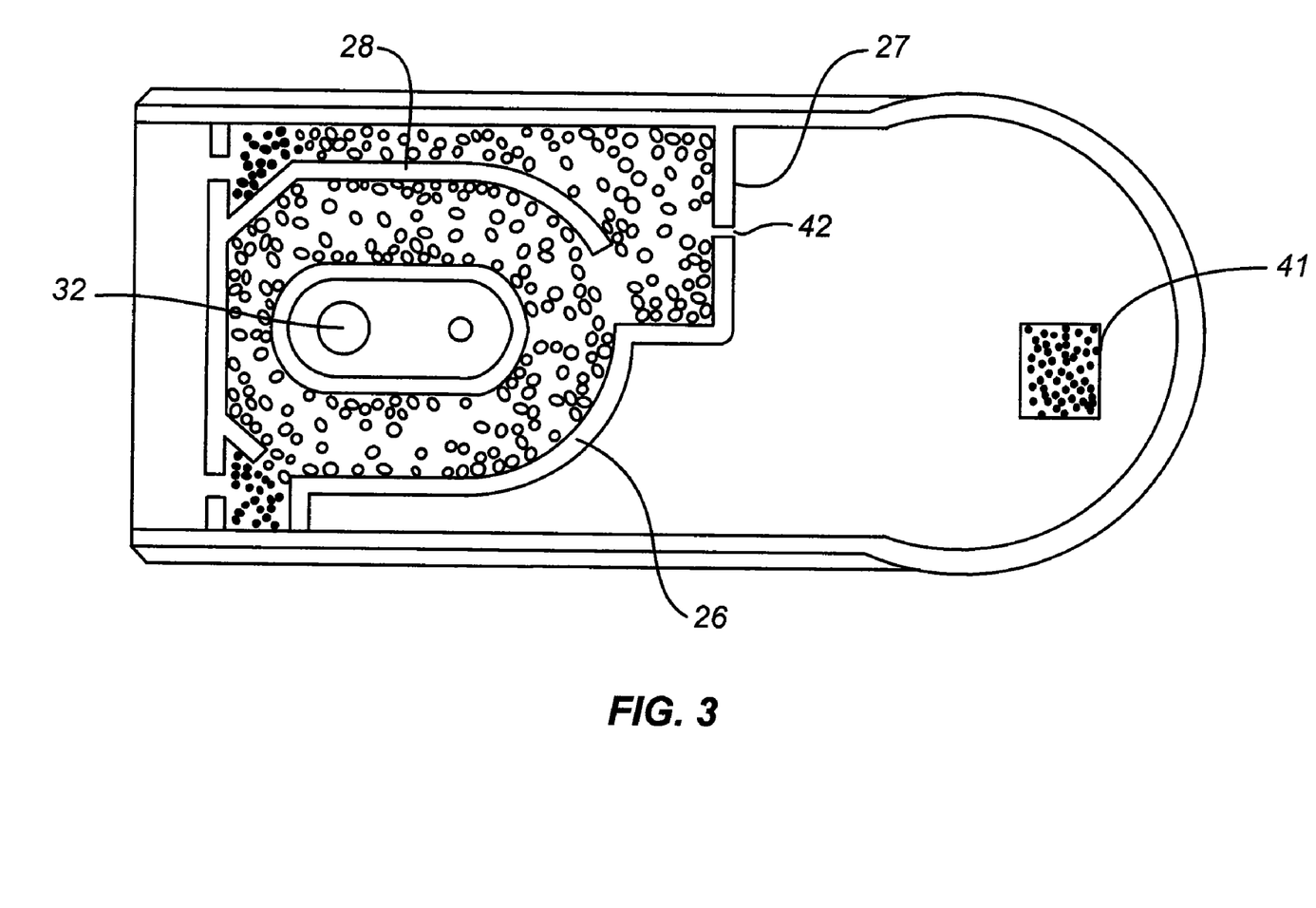
FIG. 3 is a planar view of a second device in accordance with the present invention.
Figure 4:
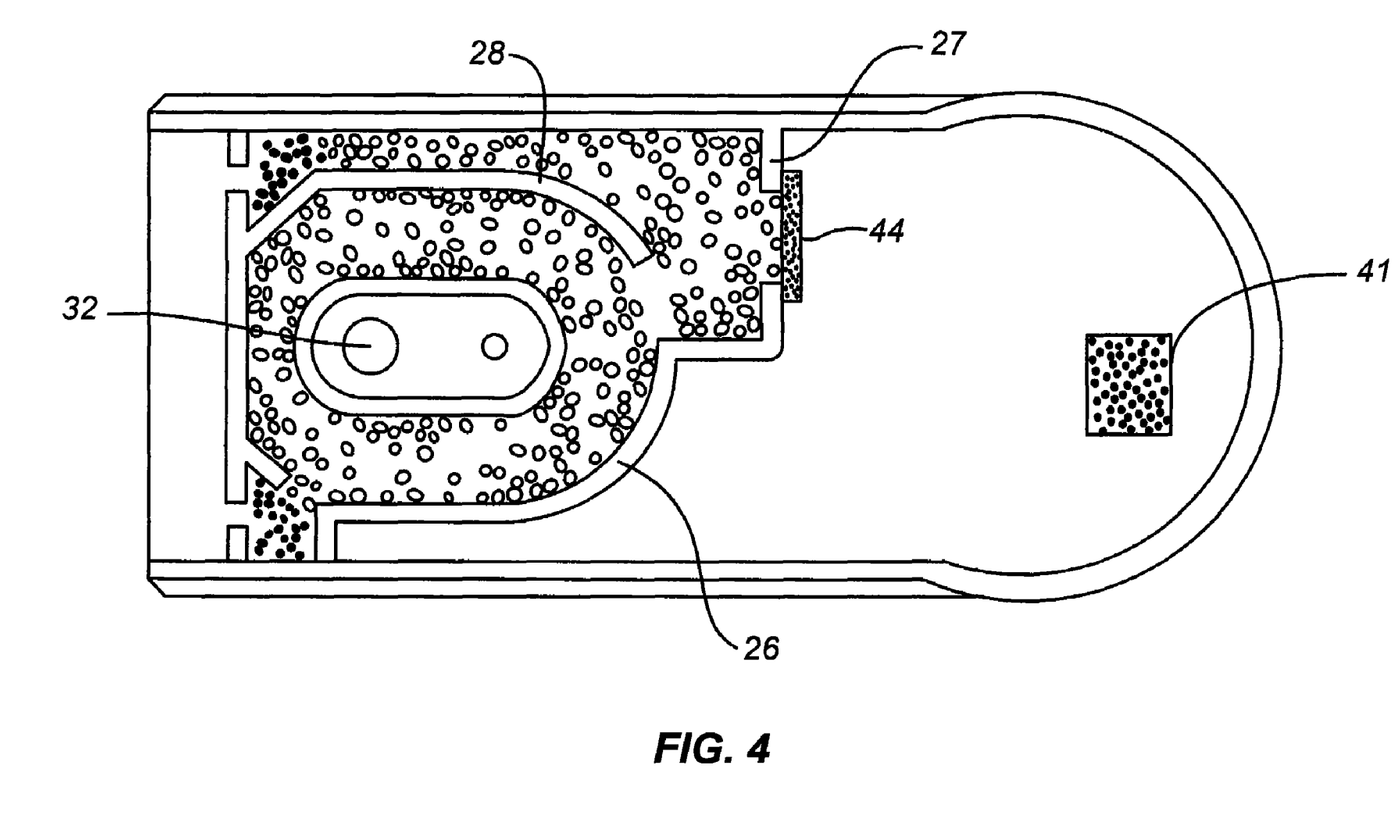
FIG. 4 is a planar view of a third device in accordance with the present invention.
Figure 5:
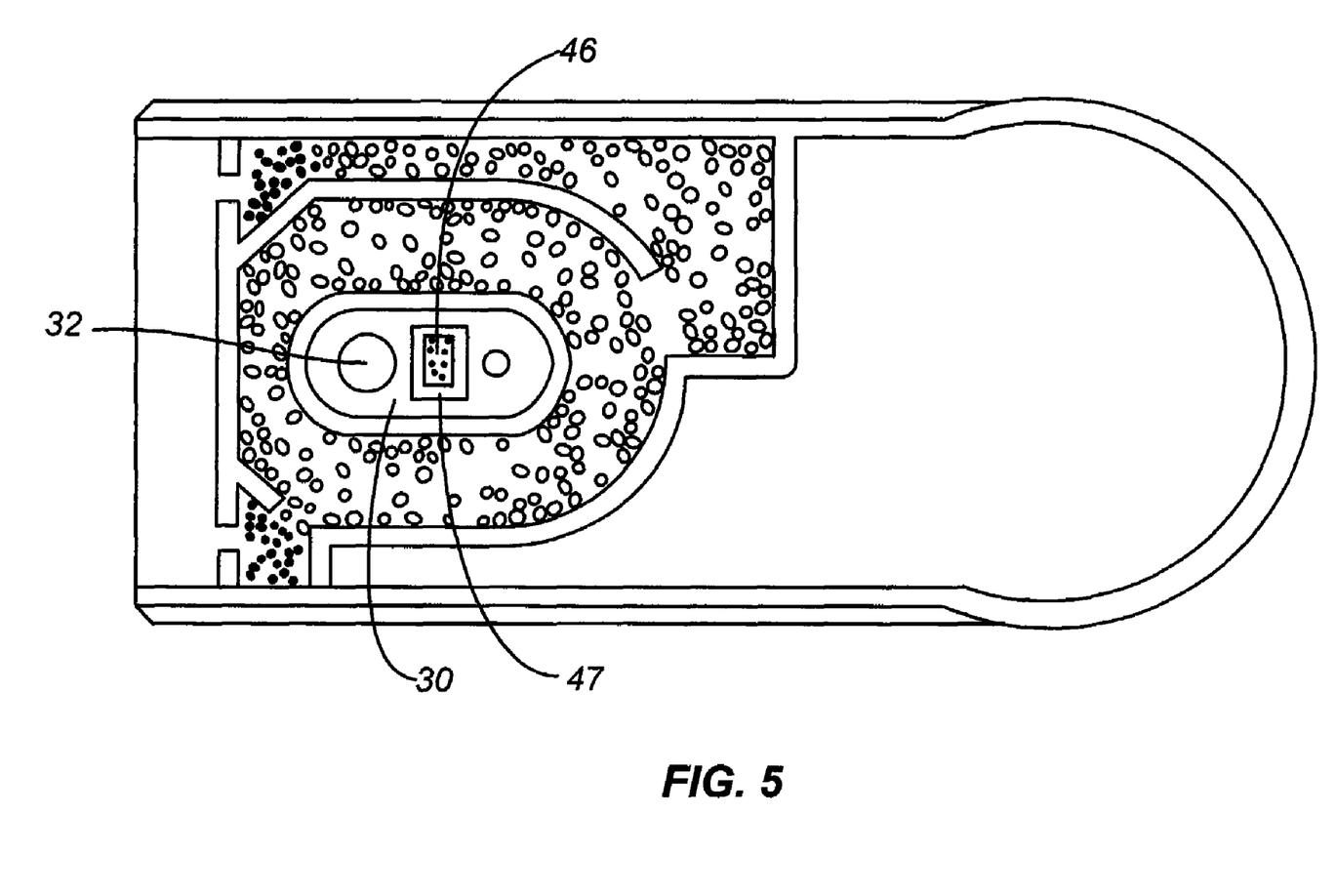
FIG. 5 is a planar view of a fourth device in accordance with the present invention.

One alternative arrangement for preventing the scavenger from drawing analyte away from the sensor, or at least for minimizing this effect is shown in FIG. 3. In this arrangement, the scavenger 41 is placed outside the outer partitions 26, 27, 28, and an orifice 42 restricts the rate of diffusion of gas between the scavenger 41 and the sensor 32. Another alternative arrangement is shown in FIG. 4, in which the orifice 42 of FIG. 3 is replaced by a membrane 44 which is permeable but permits diffusion only at a rate low enough to minimize or prevent the interference. A still further alternative is shown in FIG. 5 where the scavenger 46 is placed in the core region 30 in close proximity to the sensor but coated on all sides with a porous coating 47 that limits diffusion in a manner analogous to that of the membrane 44 of FIG. 4. Diffusion-limiting membranes and coatings are known in the art.

For analyzers designed for those suffering from asthma, the incorporation of a carbon monoxide scavenger in accordance with this invention provides these analyzers with a prolonged shelf life and the maintenance of a detection sensitivity for nitric oxide levels as low as about 1 to about 300 ppb. Analyzers for detecting nitric oxide levels in other gases, such as nasal gas or atmospheric or industrial gas, may seek to detect nitric oxide at levels up to 100 or 1,000 ppm. The shelf lives of these analyzers are likewise prolonged by the practice of this invention and their detection sensitivity is likewise maintained.

The foregoing is offered primarily for purposes of illustration. Further variations in the materials and configurations that will be readily apparent to those skilled in the art can be made while still within the scope of the invention.

What is claimed is:

1. In a device for detecting nitric oxide in a gas sample, said device comprising a sensor that binds both said nitric oxide and carbon monoxide and undergoes a detectable change when bound to said nitric oxide, said sensor retained in a housing that is constructed of or further retains a carbon monoxide-releasing material, the improvement in which said device further comprises a carbon monoxide scavenger retained within said housing or within packaging enclosing said housing and is confined to a localized region that is removed from said sensor by a distance of about 3 mm to about 300 mm, such that any variation in nitric oxide detection caused by said scavenger is less than the greater of 1 ppb of nitric oxide or 10% of the level of nitric oxide detected.

2. In a device for detecting nitric oxide in a gas sample, said device comprising a sensor that binds both said nitric oxide and carbon monoxide and undergoes a detectable change when bound to said nitric oxide, said sensor retained in a housing that is constructed of or further retains a carbon monoxide-releasing material, the improvement in which said device further comprises a carbon monoxide scavenger separated from said sensor by a flow-restricting orifice that limits any variation in nitric oxide detection caused by said scavenger to less than the greater of 1 ppb of nitric oxide or 10% of the level of nitric oxide detected.

3. In a device for detecting nitric oxide in a gas sample, said device comprising a sensor that binds both said nitric oxide and carbon monoxide and undergoes a detectable change when bound to said nitric oxide, said sensor retained in a housing that is constructed of or further retains a carbon monoxide-releasing material, the improvement in which said device further comprises a carbon monoxide scavenger separated from said sensor by a diffusion-lowering membrane that limits any variation in nitric oxide detection caused by said scavenger to less than the greater of 1 ppb of nitric oxide or 10% of the level of nitric oxide detected.

4. In a device for detecting nitric oxide in a gas sample, said device comprising a NO sensor consisting of cytochrome C encapsulated in a sol gel matrix and retained in a housing that is constructed of or further retains a carbon monoxide-releasing material, the improvement in which said device further comprises a carbon monoxide scavenger retained within said housing or within packaging enclosing said housing.

5. The device of claims 1, 2, 3, or 4 wherein said carbon monoxide scavenger is a transition metal oxide that causes the oxidation of carbon monoxide.

6. The device of claims 1, 2, 3, or 4 wherein said carbon monoxide scavenger is a member selected from the group consisting of manganese dioxide, cupric oxide, and nickel oxide, and mixtures thereof.

7. The device of claims 1, 2, 3, or 4 wherein said carbon monoxide scavenger is a mixture of manganese dioxide and cupric oxide.

8. The device of claims 1, 2, 3, or 4 wherein said carbon monoxide-releasing material is a polymeric material incorporated in said housing.

9. The device of claims 1, 2, 3, or 4 wherein said carbon monoxide-releasing material is a member selected from the group consisting of an acrylic resin and a polycarbonate.

10. The device of claims 1, 2, 3, or 4 wherein said carbon monoxide-releasing material is an acrylic resin.

11. The device of claims 1, 2, 3, or 4 wherein said carbon monoxide scavenger is a metal or metal oxide that causes the oxidation of carbon monoxide.

12. The device of claims 1, 2, 3, or 4 wherein said carbon monoxide-releasing material is a polymeric material incorporated in said housing and said carbon monoxide scavenger is a granulated solid that constitutes from about 0.005 to about 0.3 part by weight of scavenger per 100 parts by weight of said polymeric material.

13. The device of claims 1, 2, 3, or 4 wherein said carbon monoxide-releasing material is a polymeric material incorporated in said housing and wherein said carbon monoxide scavenger is a granulated solid that constitutes from about 0.01 to about 0.1 part by weight of scavenger per 100 parts by weight of said polymeric material.

14. The device of claim 1 wherein said localized region is from about 3 mm to about 300 mm from said sensor.

15. The device of claim 1 wherein said localized region is from about 10 mm to about 100 mm from said sensor.

* * * * *